US00PP15782P3

(12) United States Plant Patent
Kagan

(10) Patent No.: US PP15,782 P3
(45) Date of Patent: Jun. 7, 2005

(54) ***GLOBULARIA* PLANT NAMED 'HIS EYEBALL COMP'**

(50) Latin Name: *Globularia arabica*
Varietal Denomination: His Eyeball Comp

(75) Inventor: David Kagan, Moshav Sitriya (IL)

(73) Assignee: Hishtil Afula Ltd., Afula (IL)

( * ) Notice: Subject to any disclaimer, the term of this patent is extended or adjusted under 35 U.S.C. 154(b) by 0 days.

(21) Appl. No.: 10/298,721

(22) Filed: Nov. 18, 2002

(65) Prior Publication Data

US 2004/0098774 P1 May 20, 2004

(51) Int. Cl.[7] ..... A01H 5/00
(52) U.S. Cl. ..... Plt./226

(58) Field of Search ..... Plt./226

(56) References Cited

PUBLICATIONS http://www.arabmab.net/florainfo.cfm?fid=77.*
http://www.botanic.co.il/a/catalog.asp?qcat=GLOARA.*
UPOV ROM GTITM Computer Database, GTI Jouve Retrieval Software 2003/05 Citations For 'His Eye Ball'.*

* cited by examiner

*Primary Examiner*—Bruce R. Campell
*Assistant Examiner*—W C Haas
(74) *Attorney, Agent, or Firm*—Webb Ziesenheim Logsdon Orkin & Hanson, P.C.

(57) ABSTRACT

A new and distinct *Globularia arabica* Jaub. et Sp. plant with a compact growth habit and dark blue flowers suitable for use as a potted plant.

2 Drawing Sheets

Botanical classification: *Globularia arabica* Jaub. et Sp.
Varietal denomination: 'His Eyeball Comp'.

BACKGROUND OF THE INVENTION

The present invention comprises a new and distinct cultivar of *Globularia arabica* Jaub. et Sp. known by the varietal name 'His Eyeball Comp'. The new variety was discovered in a planned breeding program conducted by the inventor in Moshav Sattarya, located in the central Coastal Plain, Israel.

'His Eyeball Comp' originated as a single plant from a cross made by the inventor of a *globularia* selection identified as 'B-5', not patented, (female parent), with a *globularia* selection identified as '21/5', not patented, as male parent. The new *globularia* was selected by the inventor from the seedling population obtained from this cross in 1996 on the basis of its particular compact growth habit, making it suitable as a pot plant.

Asexual propagation of the new plant by terminal cuttings since 1997 has shown that the unique features of the new *globularia* are stable and propagated true to type in successive generations. The phenotype may vary somewhat due to variation in environment, such a temperature, light intensity, daylength, or fertility level of soil. As *globularia* can be rooted easily in various environments, no specific conditions for its propagation are required.

DESCRIPTION OF THE DRAWINGS

The accompanying photographic drawings illustrate the new variety, with the colors being as nearly true as is possible with color illustrations of this type.

DESCRIPTION OF THE PLANT

Figure 1:
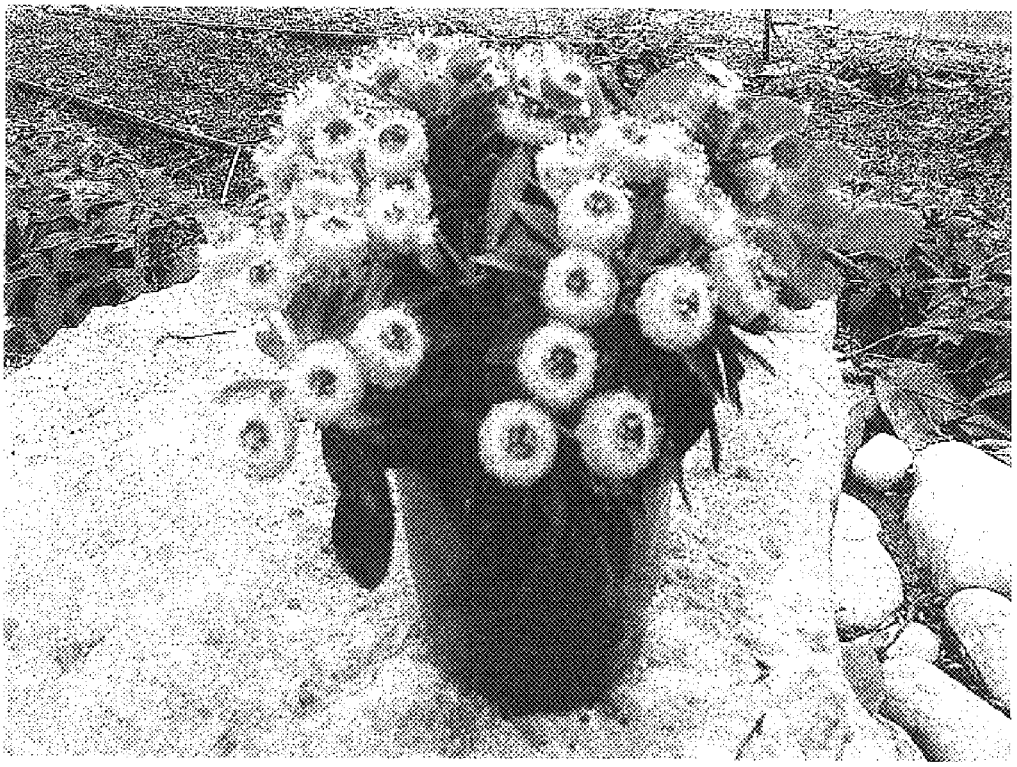
FIG. 1 shows a whole plant of the claimed variety.
Figure 2:
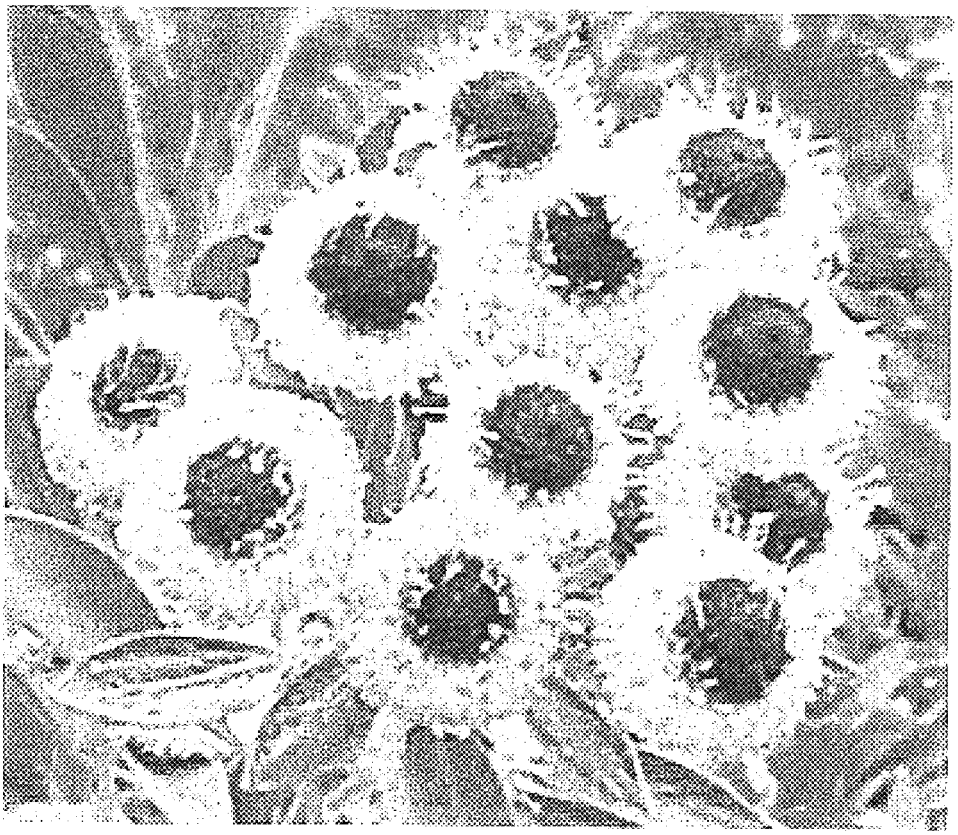
FIG. 2 shows a close-up view of the flowers and leaves of the claimed variety.

The following detailed description sets forth the characteristics of the new variety. The data which defines these characteristics were collected by asexual reproductions by cuttings carried out in Sattarya, Israel. The new variety is an ornamental perennial shrub and grows well in sandy soils, open fields, or a greenhouse. The new variety was two (2) years old when described and was grown in an open field in a Mediterranean climate. Color references are primarily to The R.H.S. Colour Chart of The Royal Horticultural Society of London.

PLANT

Growth habit: Bushy.
Height: Approximately 20 cm at 2 years.
Width: Approximately 30 cm at 2 years.
Growth: Vigorous; slow growth rate; similar to tree growth.
Branching: Basal, with approximately 30 branches on a 2 year old plant grown in an open field.
Flowering habit: Continuous.
Natural flowering season: Spring-summer. If flowers are planted I October, the first flowering occurs in Spring approximately 6 months later. The duration of flowering is 2 months.
Stems:
- *Appearance.*—Weedy.
- *Length.*—15–30 cm.
- *Node length.*—3–15 mm.
- *Thickness.*—Approximately 3 mm.
- *Texture.*—Slightly tribbed.
- *Shape.*—Round.
- *Color.*—144D.
- *Pubescence.*—Glabrous.
- *Prickles.*—None.

Leaves:
*Average number.*—Approximately 100 leaves on a 2 year old plant grown in an open field.
*Arrangement.*—Alternate.
*Composition.*—Simple.
*Length.*—60–70 mm.
*Width.*—15–20 mm.
*Texture.*—Smooth.
*Surface of upper side.*—Glabrous.
*Surface of lower side.*—Glabrous.
*Shape.*—Overall: Spatulate. Tip: Apiculate. Base: Tapering. Cross section: Straight. Longitudinal axis: Straight.
*Margin.*—Entire; very slight.
*Color.*—Upper surface (young): 147B. Lower surface (young): 147B. Upper surface (mature): 147A. Lower surface (mature): 147A. Veins (upper and lower surface): Main vein somewhat lighter.
*Petioles.*—Length: Sessile.
*Stipules.*—Not present.

Inflorescence:
*Type.*—Complex corymb.
*Length.*—5–6 cm.
*Width.*—7–8 cm.
*Number of flower heads.*—3 to 7.

Flower head just before opening of florets:
*Shape.*—Slightly domed.
*Height.*—6 mm.
*Width.*—10 mm.
*Color.*—103A.

Flower head with several whorls open:
*Opening.*—From outside.
*Duration.*—Approximately 10 days.
*Fragrance.*—None.
*Height.*—10 mm.
*Diameter.*—20 mm.
*Number of florets.*—Numerous; approximately 30 per flower head.
*Number of sepals.*—None.

Floret:
*Type.*—Labiate.
*Shape.*—Zygomorphic.
*Lip.*—Color: White. Length: Approximately 5 mm. Width: Approximately 4 mm. Distal part of limb: 3-lobed.
*Tube.*—Shape of tube: Funnel. Length of tube: Approximately 3 mm. Color of tube: White.
*Number of stamen.*—Four.
*Number of styles.*—One.

Bract:
*Number.*—30.
*Shape.*—Ovate.
*Length.*—5 mm.
*Width.*—Approximately 1 mm.
*Color.*—Light green.
*Pubescence.*—Very strong.

Peduncle:
*Length.*—35–40 mm.
*Thickness.*—1.5 mm.
*Color.*—147C.
*Pubescence.*—Very strong.

Stamen:
*Length.*—6 mm.
*Color.*—White.

Anther:
*Length.*—Approximately 1 mm.
*Color.*—Light yellow.
*Color of pollen.*—Light yellow.

Style:
*Length.*—Approximately 1 mm.
*Color.*—White.

Stigma:
*Color.*—White.

Seed:
*Length.*—Approximately 0.7 mm.
*Width.*—Approximately 0.5 mm.
*Color.*—Nearly black.
*Shape.*—Round to elliptic.

Root:
*System.*—Spreading.

Heat tolerance: Up to 40° C.
Cold tolerance: Down to 0° C.

I claim:

1. A new and distinct variety of *Globularia arabica* Jaub. et Sp. plant substantially as shown and described.

* * * * *